(12) United States Patent
Nomura et al.

(10) Patent No.: US 12,674,789 B2
(45) Date of Patent: Jul. 7, 2026

(54) GAS SENSOR

(71) Applicant: Niterra Co., Ltd., Nagoya-shi (JP)

(72) Inventors: Masashi Nomura, Nagoya-shi (JP);
Motohiko Nakamura, Nagoya-shi (JP);
Hidenari Matsumoto, Nagoya-shi (JP)

(73) Assignee: Niterra Co., Ltd., Nagoya (JP)

( * ) Notice: Subject to any disclaimer, the term of this patent is extended or adjusted under 35 U.S.C. 154(b) by 314 days.

(21) Appl. No.: 18/323,479

(22) Filed: May 25, 2023

(65) Prior Publication Data

US 2023/0393109 A1 Dec. 7, 2023

(30) Foreign Application Priority Data

Jun. 1, 2022 (JP) ................................. 2022-089590

(51) Int. Cl.
*G01N 15/06* (2024.01)
*G01N 27/409* (2006.01)
*G01N 27/419* (2006.01)
*G01N 33/00* (2006.01)

(52) U.S. Cl.
CPC ..... *G01N 33/0027* (2013.01); *G01N 15/0656* (2013.01); *G01N 27/409* (2013.01); *G01N 27/419* (2013.01)

(58) Field of Classification Search
CPC ........... G01N 33/0027; G01N 15/0656; G01N 27/409; G01N 27/419; G01N 27/4062; G01N 27/407; G01N 27/4071
See application file for complete search history.

(56) References Cited

U.S. PATENT DOCUMENTS

| | | | |
|---|---|---|---|
| 5,859,361 A | * | 1/1999 | Fukaya ................ G01N 27/407 |
| | | | 427/372.2 |
| 5,874,664 A | * | 2/1999 | Watanabe .......... G01N 27/4078 |
| | | | 73/23.32 |
| 10,598,628 B2 | * | 3/2020 | Nagata ................. G01N 27/304 |

(Continued)

FOREIGN PATENT DOCUMENTS

| | | |
|---|---|---|
| JP | 2015-152465 A | 8/2015 |
| JP | 2017-194355 A | 10/2017 |

OTHER PUBLICATIONS

Office Action dated Oct. 7, 2025 in Japanese Application No. 2022-089590.

*Primary Examiner* — David J Bolduc
(74) *Attorney, Agent, or Firm* — Sughrue Mion, PLLC

(57) ABSTRACT

A gas sensor (1) including: a sensor element (5) having an electrode pad (31, 32, 34, 35); a metallic terminal member (41) electrically connected to the electrode pad; and a lead wire (37) electrically connected to the metallic terminal member. The metallic terminal member has a forward-end-side terminal portion (43) which comes into contact with the electrode pad and a rear-end-side terminal portion (45) which is connected to the lead wire. The forward-end-side terminal portion has a bent portion (43d), and an element contact portion (43e) which comes into contact with the electrode pad. The rear-end-side terminal portion has a crimp terminal portion (45a) which forms a tube or a part of a tube, surrounds a conductor (37a) of the lead wire, and fixedly holds the conductor when crimped. Further, the maximum thickness t1 of the bent portion is greater than a maximum thickness t2 of the crimp terminal portion.

3 Claims, 4 Drawing Sheets

(56)         References Cited

U.S. PATENT DOCUMENTS

| | | | |
|---|---|---|---|
| 2005/0028581 A1* | 2/2005 | Tsuji | G01N 27/4071 |
| | | | 73/23.31 |
| 2006/0220159 A1* | 10/2006 | Matsuo | G01N 27/407 |
| | | | 257/414 |
| 2007/0128955 A1* | 6/2007 | Nishio | H01R 13/03 |
| | | | 439/877 |
| 2009/0223818 A1* | 9/2009 | Matsui | G01N 27/4062 |
| | | | 204/412 |
| 2010/0139379 A1* | 6/2010 | Kume | G01N 27/4062 |
| | | | 73/114.73 |
| 2011/0017596 A1* | 1/2011 | Kamiya | G01N 27/407 |
| | | | 419/38 |
| 2012/0097537 A1* | 4/2012 | Matsui | G01N 27/4062 |
| | | | 204/406 |
| 2014/0299469 A1* | 10/2014 | Oba | G01N 27/407 |
| | | | 204/412 |
| 2014/0302726 A1* | 10/2014 | Adachi | G01N 27/4062 |
| | | | 29/863 |
| 2014/0339081 A1* | 11/2014 | Tahira | G01N 27/407 |
| | | | 204/424 |
| 2017/0307478 A1* | 10/2017 | Oba | G01N 27/4062 |
| 2019/0285578 A1* | 9/2019 | Mihara | G01N 27/4077 |
| 2021/0041393 A1* | 2/2021 | Liu | G01N 27/407 |
| 2021/0349051 A1* | 11/2021 | Okai | G01N 27/4062 |

* cited by examiner

GAS SENSOR

BACKGROUND OF THE INVENTION

1. Field of the Invention

The present invention relates to a gas sensor which includes a sensor element for detecting the concentration of a gas to be detected and metallic terminal members.

2. Description of the Related Art

A gas sensor which includes a plate-shaped sensor element formed of solid electrolyte has been known as a gas sensor for detecting the concentration of oxygen or NOx in exhaust gas discharged from an automobile or the like.

In a widely used gas sensor of this type, a plurality of electrode pads are provided in rear-end-side zones of opposite main faces of the plate-shaped sensor element. Further, metallic terminal members are electrically contacted with the respective electrode pads so as to output a sensor output signal from the sensor element to the outside and supply electric current to a heater stacked on the sensor element (see Patent Document 1).

Each of the metallic terminal members has a forward-end-side terminal portion which comes into contact with an electrode pad, and a rear-end-side terminal portion which is connected to a lead wire. The lead wire extends to the outside of the gas sensor.

[Patent Document 1] Japanese Patent Application Laid-Open (kokai) No. 2015-152465

Incidentally, the forward-end-side terminal portion has a bent-back (bent) portion, and the bent-back portion resiliently deforms thereby securing the contact pressure applied to the electrode pad. Therefore, there is a need to provide a forward-end-side terminal portion having high strength and resilience.

Meanwhile, the rear-end-side terminal portion is a crimp terminal portion (crimp portion) which grasps the conductor of a lead wire. Further, there is a need to provide the rear-end-side terminal portion with a small degree of spring back so that the crimped portion does not deform reversely after crimping. Therefore, the rear-end-side terminal portion must have characteristics contrary to those of the forward-end-side terminal portion.

However, since metallic terminal members used in a conventional gas sensor are formed such that the forward-end-side terminal portion and the rear-end-side terminal portion have the same thickness, it is difficult for metallic terminal members to simultaneously have a sufficient degree of resilience and proper crimping characteristics.

SUMMARY OF THE INVENTION

In view of the forgoing, an object of the present invention is to provide a gas sensor in which metallic terminal members simultaneously have a sufficient degree of resilience and proper crimping characteristics and can be electrically connected, without fail, to electrode pads of a sensor element and lead wires.

The above object of the present invention has been achieved by providing (1) a gas sensor comprising: a sensor element extending in an axial direction and having an electrode pad on a rear-end-side outer surface thereof; a metallic terminal member electrically connected to the electrode pad; and a lead wire electrically connected to the metallic terminal member, wherein the metallic terminal member has a forward-end-side terminal portion which comes into contact with the electrode pad and a rear-end-side terminal portion which is connected to the lead wire, the forward-end-side terminal portion has a bent portion bent toward the sensor element, and an element contact portion which is integrally connected to the bent portion, extends toward the sensor element, and comes into contact with the electrode pad, the rear-end-side terminal portion has a crimp terminal portion which forms a tube or a part of a tube, surrounds a conductor of the lead wire, and fixedly holds the conductor when crimped, and a maximum thickness t1 of the bent portion is greater than a maximum thickness t2 of the crimp terminal portion.

In the above gas sensor (1), since the maximum thickness t1 is greater than the maximum thickness t2, the bent portion has increased resilience, whereby the contact pressure between the element contact portion and the electrode pad can be secured stably. As a result, the metallic terminal member and the electrode pad can be electrically connected in a reliable manner.

Also, by rendering the thickness t2 smaller than the thickness t1, it is possible to reduce the thickness t2 while increasing the resilience of the bent portion. Thus, the degree of spring back of the crimp terminal portion which surrounds the conductor of the lead wire and is crimped decreases, whereby crimping characteristics are improved. As a result, the metallic terminal member and the lead wire can be electrically connected without fail. In the above-described manner, the metallic terminal member can simultaneously have a sufficient degree of resiliency and proper crimping characteristics.

In a preferred embodiment (2) of the gas sensor (1) of the present invention, the forward-end-side terminal portion and the rear-end-side terminal portion are separate members and connected to each other.

According to the above gas sensor (2), the forward-end-side terminal portion and the rear-end-side terminal portion having different thicknesses can be produced easily.

In another preferred embodiment (3) of the gas sensor (1) of the present invention, the maximum thickness t1 of the bent portion is 15% or more greater than the maximum thickness t2 of the crimp terminal portion.

The present invention can provide a gas sensor in which metallic terminal members simultaneously have a sufficient degree of resilience and proper crimping characteristics, and which can be electrically connected, without fail, to electrode pads of a sensor element and lead wires.

DESCRIPTION OF REFERENCE NUMERALS

Figure 1:
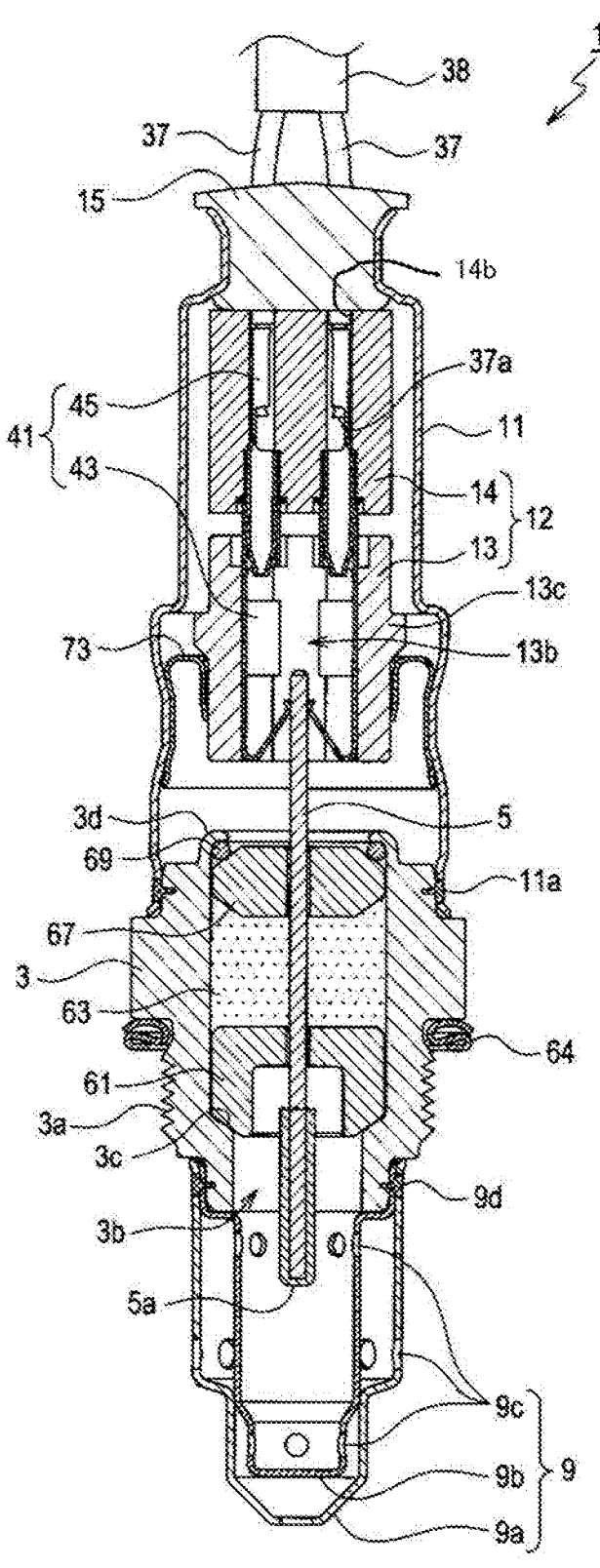
FIG. 1 is a sectional view of a gas sensor according to an embodiment of the present invention, taken along an axial direction.

Reference numerals used to identify various features in the drawings include the following.

1 gas sensor
5 sensor element
31, 32, 34, 35 electrode pad
37 lead wire
37a conductor

41 metallic terminal member
43 forward-end-side terminal portion
43*d* bent portion
43*e* element contact portion
45 rear-end-side terminal portion
45*a* crimp terminal portion

DETAILED DESCRIPTION OF THE PREFERRED EMBODIMENTS

An embodiment of the present invention will now be described with reference to the drawings. However, the present invention should not be construed as being limited thereto.

Figure 2:
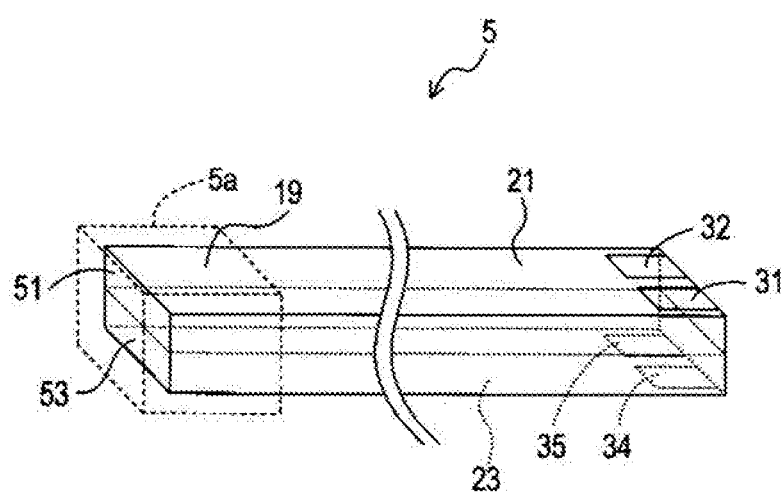
FIG. 2 is a perspective view of a sensor element.
Figure 3:
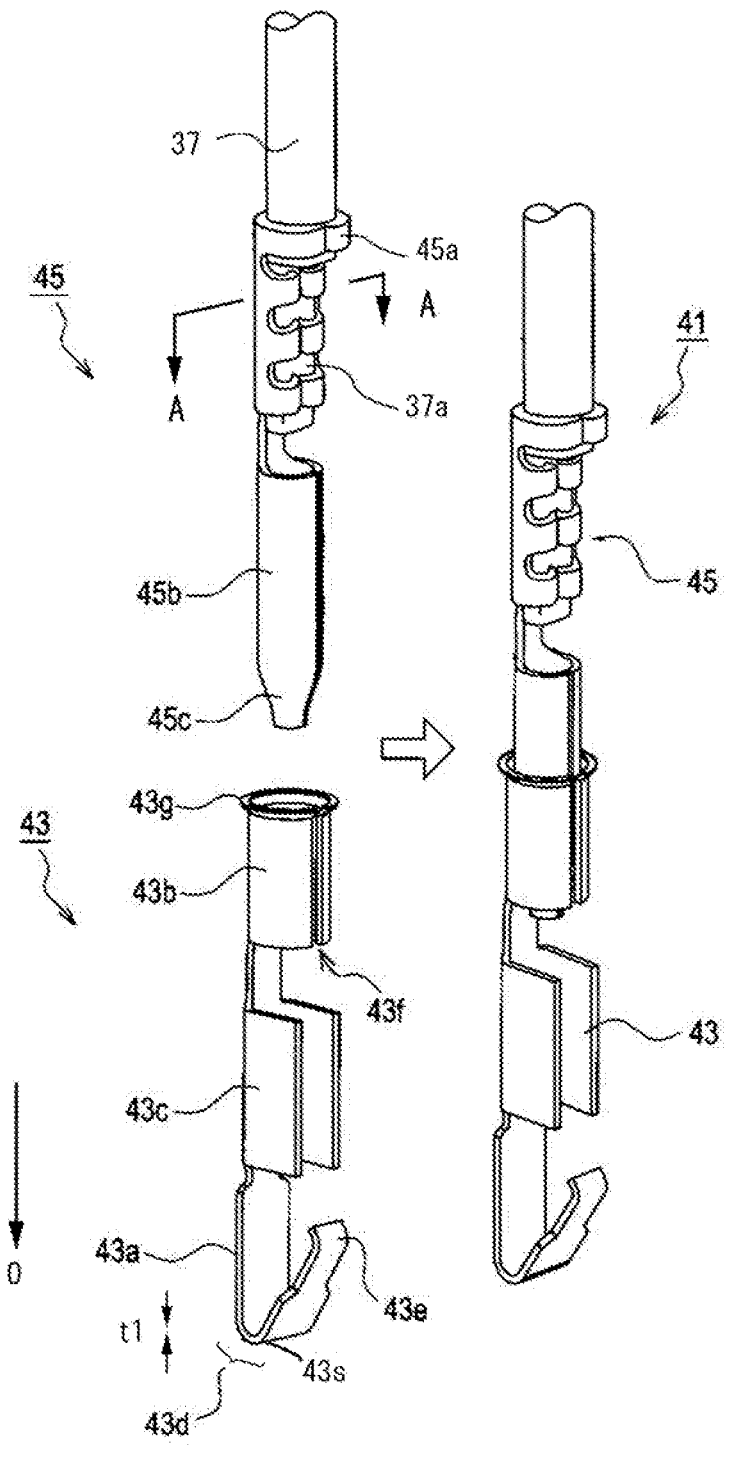
FIG. 3 is a perspective view of a metallic terminal member.
Figure 4:
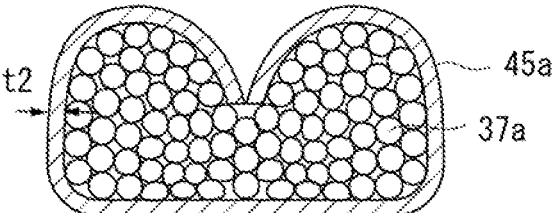
FIG. 4 is a sectional view taken along line A-A of FIG. 3.

FIG. 1 is a sectional view of a gas sensor (oxygen sensor) 1 according to an embodiment of the present invention, taken along an axial direction. FIG. 2 is a perspective view of a sensor element 5. FIG. 3 is a perspective view of a metallic terminal member 41. FIG. 4 is a sectional view taken along line A-A of FIG. 3.

In FIG. 1, a lower side of the drawing corresponds to a forward end side of the gas sensor, and an upper side of the drawing corresponds to a rear end side of the gas sensor.

The gas sensor 1 is mounted on, for example, an exhaust pipe of a vehicle such as an automobile or a motorcycle.

The gas sensor 1 includes a tubular metallic shell 3 which is fixed to the exhaust pipe (not shown); a plate-shaped sensor element 5 which penetrates the metallic shell 3 and extends in the axial direction (the longitudinal direction of the gas sensor 1: the vertical direction in the drawing); an element protector 9 which is disposed on the forward end side (the lower side in the drawing) of the metallic shell 3 and covers a forward-end-side portion of the sensor element 5; an outer casing 11 which is attached to an end of the metallic shell 3 on the rear end side (the upper side in the drawing) by a welding portion 11*a* and covers the circumference of the sensor element 5; an insulating separator 12 which is disposed in the outer casing 11 and accommodates a rear-end-side portion of the sensor element 5; a closing member 15 which closes a rear-end-side portion of the outer casing 11; a plurality of (four in the present embodiment) metallic terminal members 41, and a plurality of (four in the present embodiment) lead wires 37.

The sensor element 5 has a detection portion 19 and electrode pads (first to fourth electrode pads) 31, 32, 34, and 35. The detection portion 19 is formed in a forward-end-side portion of the sensor element 5, which portion is exposed to a measurement target (exhaust gas or the like) and is covered with a protection layer 5*a*. The electrode pads 31, 32, 34, and 35 are formed on an outer surface of a rear-end-side portion of the sensor element 5; specifically, on a first plate surface 21 and a second plate surface 23, which are a front side portion and a back side portion of the outer surface, respectively.

The sensor element 5 is fixedly disposed in the metallic shell 3 in a state in which the detection portion 19 on the forward end side projects from the forward end of the metallic shell 3, which is fixed to the exhaust pipe, and the electrode pads 31, 32, 34, and 35 on the rear end side project from the rear end of the metallic shell 3.

Metallic terminal members 41 are individually connected to the electrode pads 31, 32, 34, and 35. Namely, the plurality of metallic terminal members 41 are disposed in the insulating separator 12 so to be located between the sensor element 5 and the insulating separator 12, whereby the metallic terminal members 41 are electrically connected to the electrode pads 31, 32, 34, and 35 of the sensor element

5. Each of the metallic terminal members 41 has a forward-end-side terminal portion 43 and a rear-end-side terminal portion 45.

The plurality of metallic terminal members 41 are individually and electrically connected to a plurality of lead wires 37 (specifically, the conductors 37*a* of the lead wires 37), which are disposed to extend from the outside to the interior of the gas sensor 1.

Notably, the structure of the metallic terminal members 41 will be described in detail below.

The metallic terminal members 41 and the lead wires 37 form current paths for electric currents which flow between the sensor element 5 (specifically, the electrode pads 31, 32, 34, and 35) and an external apparatus (not shown) to which the lead wires 37 are connected. The plurality of lead wires 37 are bundled by a tube member 38. Notably, in FIG. 1, of the plurality of lead wires 37, only two lead wires 37 are shown.

FIG. 2 is a perspective view schematically showing the structure of the sensor element 5. Notably, in FIG. 2, the sensor element 5 is depicted with its intermediate portion in the axial direction being omitted.

As shown in FIG. 2, the sensor element 5 has the shape of a rectangular parallelopiped and is formed by stacking a plate-shaped element portion 51 extending in the axial direction (the horizontal direction in FIG. 2) and a plate-shaped heater 53 extending in the axial direction. The sensor element 5 has a rectangular sectional shape, when taken perpendicularly to the axial direction. In FIG. 2, the protection layer 5*a* is represented by broken lines.

Notably, since the sensor element 5 provided in the gas sensor 1 is well known, its internal structure, etc. will be not described in detail. However, the internal structure of the sensor element 5 will be described briefly.

The element portion 51 includes, for example, an oxygen concentration cell in which porous electrodes are formed on opposite sides of a solid electrolyte substrate, and a spacer for forming a hollow reference gas chamber. The solid electrolyte substrate is formed of, for example, zirconia solid solution containing yttria as a stabilizer, and the porous electrodes are formed of, for example, mainly Pt.

The spacer for forming a hollow reference gas chamber is formed of mainly alumina. One porous electrode of the oxygen concentration cell is disposed in the hollow reference gas chamber such that the porous electrode is exposed. The spacer is formed such that the reference gas chamber is located at least on the forward end side of the element portion 51. The spacer has a gas passage for introducing a reference gas (for example, atmosphere) from the outside into the reference gas chamber.

Of the element portion 51, a portion where the porous electrodes and the reference gas chamber are formed corresponds to the detection portion 19.

The heater 53 includes a pair of insulating substrates formed of mainly alumina, and a heating resistor trace formed of mainly Pt and sandwiched between the insulating substrates. The element portion 51 and the heater 53 are joined to each other via a ceramic layer (formed of, for example, zirconia-based ceramic material or alumina-based ceramic material).

The sensor element 5 has the protection layer 5*a* (not shown in FIG. 2) which is formed of a porous ceramic material for preventing poisoning. The protection layer 5*a* is provided at least on the surfaces of the electrode which is located on the forward end side and is exposed to a gas to be measured (in the present embodiment, exhaust gas). Notably, in the sensor element 5 of the present embodiment, as shown in FIG. 1, the protection layer 5*a* covers the entire surface of a forward-end-side portion of the sensor element 5, which includes the surfaces of the porous electrode exposed to exhaust gas.

In such a sensor element 5, as shown in FIG. 2, two electrode pads 31 and 32 are formed on the rear end side (the right side in FIG. 2) of the first plate surface 21, and two electrode pads 34 and 35 are formed on the rear end side of the second plate surface 23. The electrode pads 31 and 32 are formed on the element portion 51 and are electrically connected to the pair of porous electrodes of the oxygen concentration cell. The electrode pads 34 and 35 are formed on the heater 53 and are individually connected to opposite ends of the heating resistor trace through via conductors (not shown) which extend through the heater 53 in the thickness direction.

Referring back to FIG. 1, the metallic shell 3 is a tubular member which has a screw portion 3*a* formed on its outer surface and a through hole 3*b* at its axial center. The screw portion 3*a* is used for fixing the metallic shell 3 to the exhaust pipe. A ledge portion 3*c* projecting radially inward is formed in the through hole 3*b*. The metallic shell 3 is formed of a metallic material (for example, stainless steel).

Within the through hole 3*b* of the metallic shell 3, an annular holder 61 (ceramic holder 61), an annular powder-charged layer 63 (talc ring 63), and an annular sleeve 67 (ceramic sleeve 67) are stacked in this order from the forward end side toward the rear end side. The holder 61 is formed of an insulating material (for example, alumina) and is disposed to surround the circumference of the sensor element 5. The powder-charged layer 63 is similarly disposed to surround the circumference of the sensor element 5. The sleeve 67 is formed of an insulating material (for example, alumina) and is similarly disposed to surround the circumference of the sensor element 5.

A crimp packing 69 is disposed between the ceramic sleeve 67 and a rear end portion 3*d* of the metallic shell 3. Notably, the rear end portion 3*d* of the metallic shell 3 is crimped such that the rear end portion 3*d* presses the ceramic sleeve 67 toward the forward end side via the crimp packing 69.

An annular gasket 64 is disposed on the outer circumference of the metallic shell 3 so to be located on the rear end side of the screw portion 3*a*. The gasket 64 prevents leakage of gas through the gap between the gas sensor 1 and the member (the exhaust pipe) to which the sensor is attached.

The element protector 9 is a tubular member attached to the outer circumference of a forward-end-side portion of the metallic shell 3 by a welded portion 9*d* such that the element protector 9 covers a projecting portion of the sensor element 5. The element protector 9 is formed of a heat-resisting material (for example, SUS310S or the like). The element protector 9 has a double structure including an outer protector 9*a* and an inner protector 9*b*. Each of the outer protector 9*a* and the inner protector 9*b* has a plurality of holes 9*c* formed in the side wall and/or at the forward end. The gas can pass through the holes 9*c*.

The insulating separator 12 is composed of a forward-end-side separator 13 and a rear-end-side separator 14, which can be separated from each other.

The forward-end-side separator 13 is a tubular member formed of an insulating material (for example, alumina or the like) and is held in the outer casing 11 by a tubular metal holder 73 disposed in the outer casing 11. The forward-end-side separator 13 has a terminal receiving hole 13*b* which penetrates the forward-end-side separator 13 in the axial direction. The terminal receiving hole 13*b* receives a rear end portion of the sensor element 5 (the electrode pads 31, 32, 34, and 35) and forward end portions (specifically, forward-end-side terminal portions 43) of a plurality of metallic terminal members 41 electrically connected to the electrode pads 31, 32, 34, and 35. The forward-end-side separator 13 has an annular flange portion 13*c* formed on its outer surface and projecting radially outward. The flange portion 13*c* of the forward-end-side separator 13 butts against the metal holder 73, whereby the axial position of the forward-end-side separator 13 within the outer casing 11 can be determined.

The rear-end-side separator 14 is a tubular member formed of an insulating material (for example, alumina or the like) and is disposed in the outer casing 11 so to be located on the forward end side of the closing member 15. The rear-end-side separator 14 has a plurality of terminal receiving holes 14*b* which penetrate the rear-end-side separator 14 in the axial direction. The plurality of terminal receiving holes 14*b* of the rear-end-side separator 14 individually receive rear end portions (rear-end-side terminal portions 45) of the metallic terminal members 41.

The closing member 15 is a grommet formed of a flexible member (for example, fluororesin). The closing member 15 is disposed in an opening of the outer casing 11 on the rear end side, and the outer casing 11 is crimped from the outer side toward the inner side, whereby the closing member 15 is fixed to the outer casing 11. The closing member 15 has a plurality of through holes (not shown) into which the plurality of lead wires 37 are inserted.

The plurality of lead wires 37 are connected (by means of crimping) to the rear end side portions of the different metallic terminal members 41 and extend to the outside through the through holes of the closing member 15.

Next, the metallic terminal members 41 will be described.

As described above, each metallic terminal member 41 has the forward-end-side terminal portion 43 and the rear-end-side terminal portion 45. In the present embodiment, each metallic terminal member 41 is not a single member and is formed by connecting together the forward-end-side terminal portion 43 and the rear-end-side terminal portion 45, which are separate members.

FIG. 3 is an explanatory view showing the structure of the metallic terminal member 41 having the forward-end-side terminal portion 43 and the rear-end-side terminal portion 45.

The forward-end-side terminal portion 43 is formed of a metallic material which is high in resilience (spring resilience); for example, an alloy containing Ni as a main component (NCF718 or the like).

The forward-end-side terminal portion 43 is formed by bending an elongated thin metal plate and has a main body portion 43*a*, a female-type connecting portion 43*b*, extending portions 43*c*, a bent portion 43*d*, and an element contact portion 43*e*.

The main body portion 43*a* is formed into the shape of an elongated plate extending in the axial direction.

The female-type connecting portion 43*b* is formed into a tubular shape on the rear end side of the main body portion 43*a* and has a circular sectional shape when taken perpendicularly to the axial direction. The female-type connecting portion 43*b* has a slit 43*f*. Thus, the inner diameter of the tubular female-type connecting portion 43*b* can be changed through elastic deformation. Therefore, strictly speaking, the sectional shape of the female-type connecting portion 43*b* is a circle with a break. The female-type connecting portion 43*b* has a diameter increasing portion 43*g* on the rear end side. The diameter increasing portion 43g is formed such that its diameter increases toward the rear end side.

The extending portions 43c extend, in a direction perpendicular to plate surfaces of the main body portion 43a, from the main body portion 43a at two locations; i.e., from side portions of the main body portion 43a. Since the extending portions 43c are provided, the strength of the main body portion 43a can be increased.

The bent portion 43d is integrally provided on the forward end side of the main body portion 43a. The bent portion 43d is formed through bending (bending back), on the forward end side of the main body portion 43a, in the direction perpendicular to the plate surfaces of the main body portion 43a such that the bent portion 43d extends from the rear end side to a forwardmost end 43s and then extends toward the rear end side. The bent portion 43d is a connecting portion for connecting together the main body portion 43a and the element contact portion 43e.

The element contact portion 43e, which is connected to the main body portion 43a via the bent portion 43d, is formed such that the size of the gap between the element contact portion 43e and the main body portion 43a (the distance between the element contact portion 43e and the main body portion 43a) can be changed through elastic deformation of the bent portion 43d.

The forward-end-side terminal portion 43 configured as described above can maintain the contact between the element contact portion 43e and the sensor element 5 (specifically, the electrode pad 31, 32, 34, or 35) through elastic deformation of the bent portion 43d. Namely, the contact pressure between the element contact portion 43e and the electrode pad 31, 32, 34, or 35 is secured by the elastic deformation of the bent portion 43d.

The rear-end-side terminal portion 45 is formed of, for example, a stainless alloy (SUS304). The rear-end-side terminal portion 45 is formed by bending an elongated thin metal plate and has a crimp terminal portion 45a and a male-type connecting portion 45b.

The crimp terminal portion 45a is configured such that, when it deforms as a result of bending, the crimp terminal portion 45a has a tubular shape (see FIG. 4) which can surround the conductor 37a of a lead wire 37 (see FIG. 1). The crimp terminal portion 45a is crimped radially inward in a state in which the crimp terminal portion 45a surrounds the conductor 37a of the lead wire 37, whereby the crimp terminal portion 45a is connected to the conductor 37a of the lead wire 37 mechanically and electrically.

The male-type connecting portion 45b is formed into a tubular shape on the forward end side of the crimp terminal portion 45a and has a circular sectional shape when taken perpendicularly to the axial direction. The outer diameter of the male-type connecting portion 45b is set such that the male-type connecting portion 45b can be disposed in the female-type connecting portion 43b. The male-type connecting portion 45b has a diameter reducing portion 45c on the forward end side. The diameter reducing portion 45c is formed such that its diameter decreases toward the forward end side.

The rear-end-side terminal portion 45 configured as described above is electrically connected to an external apparatus through the lead wire 37 as a result of electrical connection of the crimp terminal portion 45a to the conductor 37a of the lead wire 37.

As shown in a right-side region of FIG. 3, the metallic terminal member 41 is configured by connecting together the forward-end-side terminal portion 43 and the rear-end-side terminal portion 45. Specifically, the male-type connecting portion 45b and the female-type connecting portion 43b are connected to each other whereby the metallic terminal member 41 having the forward-end-side terminal portion 43 and the rear-end-side terminal portion 45 is formed.

In the metallic terminal member 41 having such a configuration, the element contact portion 43e of the forward-end-side terminal portion 43 is electrically connected to the sensor element 5 (specifically, the electrode pad 31, 32, 34, or 35), and the crimp terminal portion 45a of the rear-end-side terminal portion 45 is electrically connected to the external apparatus via the lead wire 37.

The maximum thickness t1 of the forwardmost end 43s of the bent portion 43d is greater than the maximum thickness t2 of the crimp terminal portion 45a in a cross section (FIG. 4) intersecting the axial direction.

Since the bent portion 43d is thick, its resilience is increased, whereby the contact pressure between the element contact portion 43e and the electrode pad 31, 32, 34, or 35 can be secured stably. As a result, the metallic terminal member 41 and the electrode pad 31, 32, 34, or 35 can be electrically connected reliably.

Notably, in the present embodiment, the forwardmost end 43s of the bent portion 43d has the maximum thickness t1.

In the case where the forward-end-side terminal portion 43 and the rear-end-side terminal portion 45 have the same thickness (t1, t2), when the thickness t1 is increased so as to increase resilience, the thickness t2 also increases, and the degree of spring back of the crimp terminal portion 45a increases.

In view of the above, the thickness t2 is rendered smaller than the thickness t1. As a result, it is possible to reduce the thickness t2 while increasing the resilience of the bent portion 43d. Thus, the degree of spring back of the crimp terminal portion 45a which surrounds the conductor 37a of the lead wire 37 and is crimped decreases, whereby crimping characteristics are improved. As a result, the metallic terminal member 41 and the lead wire 37 can be electrically connected without fail.

In the above-described manner, the metallic terminal member 41 can simultaneously have a sufficient degree of resiliency and proper crimping characteristics.

Furthermore, by rendering the thickness t2 smaller than the thickness t1, it becomes possible to decrease the thermal conductivity of the rear-end-side terminal portion 45, thereby suppressing transmission of heat from the rear-end-side terminal portion 45 to the rear end side (the closing member 15 side) of the gas sensor 1. Thus, it becomes possible to use the gas sensor 1 at higher temperatures.

Notably, the forwardmost end 43s is an approximately strip-shaped region extending in the horizontal direction in FIG. 3, and the maximum thickness t1 refers to the largest one of the thicknesses of the forwardmost end 43s measured at a plurality of locations along the strip-shaped region.

The crimp terminal portion 45a forms a portion of a tube as shown in FIG. 4, and the maximum thickness t2 refers to the largest one of the thicknesses of the crimp terminal portion 45a measured at a plurality of locations in the circumferential direction.

Although it is sufficient that the thickness t1 is greater than the thickness t2, preferably, the thickness t1 is 15% or more greater than the thickness t2. In this case, since the difference between the thickness t1 and the thickness t2 becomes larger, the metallic terminal member 41 can simultaneously have a sufficient degree of resiliency and proper crimping characteristics more reliably.

Notably, as described above, the insulating separator 12 is composed of the forward-end-side separator 13 and the rear-end-side separator 14, which can be separated from each other.

Assembly of the insulating separator 12 is performed, for example, by the following steps. First, the rear end portion of the sensor element 5 and the four forward-end-side terminal portions 43 are disposed in the terminal receiving hole 13b of the forward-end-side separator 13. Meanwhile, after inserting the lead wires 37 into the four terminal receiving holes 14b of the rear-end-side separator 14 such that the lead wires 37 project forward from the terminal receiving holes 14b of the rear-end-side separator 14, the conductor 37a of each lead wire 37 is connected (fixed) to the crimp terminal portion 45a of the corresponding rear-end-side terminal portion 45 by means of crimping.

Subsequently, the four rear-end-side terminal portions 45 are coupled with the four forward-end-side terminal portions 43 disposed in the forward-end-side separator 13, and the rear-end-side separator 14 is moved along the lead wires 37 toward the rear-end-side terminal portions 45 such that the four rear-end-side terminal portions 45 are individually received (disposed) in the terminal receiving holes 14b.

As a result of combining the forward-end-side separator 13 and the rear-end-side separator 14 by the above-described steps, the insulating separator 12 is completed.

Although an embodiment of the present invention has been described above, the present invention is not limited to the above-described embodiment and can be practiced in various forms without departing from the scope of the invention.

For example, in the above-described embodiment, the metallic terminal member 41 is composed of the forward-end-side terminal portion 43 and the rear-end-side terminal portion 45, which are separate members. However, a metallic terminal member 41 in which the forward-end-side terminal portion 43 and the rear-end-side terminal portion 45 are formed by a single member (one body) may be used.

The gas sensor to which the present invention is applied is not limited to an oxygen sensor and may be any of other gas sensors (an NOx sensor, a hydrogen sensor, etc.) which detect other types of gases, so long as the gas sensors have metallic terminal members.

The sensor element is not limited to a plate-shaped sensor element and may be a tubular sensor element.

The bent portion may have any form, so long as the bent portion has resiliency as a result of being bent from a bending reference portion (the main body portion 43a or the like) and causes the element contact portion to contact the sensor element. For example, the bent portion may be formed by being bent from the rear end side of the main body portion 43a toward the forward end.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2022-089590 filed Jun. 1, 2022, incorporated herein by reference in its entirety.

What is claimed is:

1. A gas sensor comprising:
   a sensor element extending in an axial direction and having an electrode pad on a rear-end-side outer surface thereof;
   a metallic terminal member electrically connected to the electrode pad; and
   a lead wire electrically connected to the metallic terminal member, wherein
   the metallic terminal member has a forward-end-side terminal portion which is formed of an alloy containing Ni as a main component and which comes into contact with the electrode pad, and a rear-end-side terminal portion which is formed of a stainless alloy and which is connected to the lead wire,
   the forward-end-side terminal portion has a bent portion bent toward the sensor element, and an element contact portion which is integrally connected to the bent portion, extends toward the sensor element, and comes into contact with the electrode pad,
   the rear-end-side terminal portion has a crimp terminal portion which forms a tube or a part of a tube, surrounds a conductor of the lead wire, and fixedly holds the conductor when crimped, and
   a maximum thickness t1 of the bent portion is greater than a maximum thickness t2 of the crimp terminal portion.

2. The gas sensor as claimed in claim 1, wherein the forward-end-side terminal portion and the rear-end-side terminal portion are separate members and connected to each other.

3. The gas sensor as claimed in claim 1, wherein the maximum thickness t1 of the bent portion is 15% or more greater than the maximum thickness t2 of the crimp terminal portion.

* * * * *